US012625037B2

(12) United States Patent
Pickering et al.

(10) Patent No.: US 12,625,037 B2
(45) Date of Patent: May 12, 2026

(54) SYSTEM AND A COMPUTER-IMPLEMENTED METHOD FOR DETECTING MEDICAL-DEVICE ERRORS BY ANALYZING ACOUSTIC SIGNALS GENERATED BY THE MEDICAL DEVICE'S COMPONENTS

(71) Applicants:Fresenius Medical Care Deutschland GmbH, Bad Homburg (DE); Fresenius Medical Care Holdings, Inc., Waltham, MA (US)

(72) Inventors: Aaron Pickering, Berlin (DE); Ritwika Mukherjee, Medford, MA (US); Felix Adam, Munich (DE); Marie Elisabeth Heinrich, Munich (DE); Alan Wei Min Tan, Singapore (SG); Daniel Horcher, Hallstadt (DE); Torsten Labs, Nuemberg (DE)

( * ) Notice: Subject to any disclaimer, the term of this patent is extended or adjusted under 35 U.S.C. 154(b) by 233 days.

(21) Appl. No.: 17/881,189

(22) Filed: Aug. 4, 2022

(65) Prior Publication Data

US 2024/0044747 A1     Feb. 8, 2024

(51) Int. Cl.
G01M 99/00 (2011.01)
A61M 1/14 (2006.01)
(Continued)

(52) U.S. Cl.
CPC ............ G01M 99/005 (2013.01); A61M 1/14 (2013.01); G06N 20/00 (2019.01); G16H 40/40 (2018.01); A61M 2205/3375 (2013.01)

(58) Field of Classification Search
CPC ...... G01M 99/005; G16H 40/40; G06N 20/00
See application file for complete search history.

(56) References Cited

U.S. PATENT DOCUMENTS 9,095,314 B2    8/2015  Osorio
10,976,730 B2   4/2021  Deshpande et al.
(Continued)

FOREIGN PATENT DOCUMENTS

EP        2988105       2/2016
EP        3861307       8/2021
(Continued)

OTHER PUBLICATIONS

International Search Report and Written Opinion in International Appln. No. PCT/US2023/029201, mailed Nov. 27, 2023, 13 pages.
(Continued)

*Primary Examiner* — Lam S Nguyen
(74) *Attorney, Agent, or Firm* — Fish & Richardson P.C.

(57)     ABSTRACT

A system includes a sensor element arranged to detect a spectrum of noise or vibrations of a medical device to be supervised the, a supervising element, whereby the sensor element and the supervising element may communicate with each other and thereby allow for provisioning of data corresponding to the acoustic signals, whereby the system further comprises a localized or distributed detection engine, the detection engine analyzing the data corresponding to the acoustic signals such that typical failures of each of a plurality of individual components of the medical device are distinguished, whereby the system further comprises a notification engine, the notification engine providing indications on the maintenance state of the medical device and/or one or more of the plurality of individual components of the medical device. The disclosure also pertains to a computer-implemented method for determining a maintenance state of a medical device.

20 Claims, 3 Drawing Sheets

(51) Int. Cl.
   *G06N 20/00*      (2019.01)
   *G16H 40/40*      (2018.01)

(56) References Cited

U.S. PATENT DOCUMENTS

| | | | |
|---|---|---|---|
| 11,965,859 B1 * | 4/2024 | Jenkins | G01N 29/2437 |
| 2006/0064037 A1 | 3/2006 | Shalon et al. | |
| 2006/0135907 A1 * | 6/2006 | Remde | A61M 5/16831 |
| | | | 604/67 |
| 2008/0018435 A1 | 1/2008 | Brown | |
| 2009/0082676 A1 | 3/2009 | Bennison | |
| 2011/0021967 A1 | 1/2011 | Heide et al. | |
| 2014/0018637 A1 | 1/2014 | Bennett et al. | |
| 2014/0121845 A1 | 5/2014 | Mueller | |
| 2014/0188516 A1 | 7/2014 | Kamen | |
| 2020/0219527 A1 | 7/2020 | Kogan et al. | |
| 2020/0234818 A1 | 7/2020 | Usvyat et al. | |
| 2020/0356898 A1 | 11/2020 | Claussen et al. | |
| 2022/0026879 A1 * | 1/2022 | Kale | G06N 3/088 |
| 2023/0064906 A1 | 3/2023 | Jamieson | |
| 2024/0047059 A1 | 2/2024 | Tremblay et al. | |

FOREIGN PATENT DOCUMENTS

| | | |
|---|---|---|
| JP | 2018-179863 | 11/2018 |
| JP | 2020-185124 | 11/2020 |
| WO | WO 2009/042577 | 4/2009 |
| WO | WO 2017/112591 | 6/2017 |
| WO | WO 2018/184833 | 10/2018 |
| WO | WO 2020/036091 A1 | 2/2020 |
| WO | WO 2023/178161 | 9/2023 |

OTHER PUBLICATIONS

International Preliminary Report on Patentability in International Appln. No. PCT/US2023/029201, mailed Feb. 13, 2025, 7 pages.

* cited by examiner

SYSTEM AND A COMPUTER-IMPLEMENTED METHOD FOR DETECTING MEDICAL-DEVICE ERRORS BY ANALYZING ACOUSTIC SIGNALS GENERATED BY THE MEDICAL DEVICE'S COMPONENTS

TECHNICAL FIELD

The present disclosure relates to a system and a computer-implemented method for detecting medical-device errors by analyzing acoustic signals generated by the medical device's components.

BACKGROUND

Within the medical field and in particular within the field of dialysis, a large number of medical devices are used within prolonged periods. Some of these machines may be used by individuals in a home-setting while others may be used in a care-home or in care-centers by one or more individuals.

These medical devices may be of a life-supporting nature and sometimes may be used on a regular basis such as for dialysis treatments. Failure of one or more components of the medical device may lead to a life-threatening situation for one or more concerned patients.

While newer devices are equipped with a functionality allowing to determine a maintenance status either stand-alone or in connection with a centralized infrastructure, older devices typically do not comprise such functionality.

However, there is still a large number of old devices in use. This is to some extent based on the fact that these devices may be used by a user for a long time and also on the fact that the cost of these devices are rather high.

Therefore, a need exists to provide such functionality also for older medical devices.

Even though some of these medical devices may be furnished with upgrades for their respective hardware and firmware, allowing in cooperation with further elements to share further information, it is to be noted that hardware and firmware upgrades may entail a need for a renewed validation process due to regulatory requirements for the upgraded devices to be used within the medical field.

However, such a validation process is both expensive and time consuming. In addition, it is noted that firmware upgrades usually involve high quality requirements in order to be successful and to not render the medical device useless in case of failure.

Even then it is to be noted that a firmware upgrade may not provide measured data. That is, while a firmware upgrade may provide data, e.g., relating to the speed of a motor, such information may not be sufficient to determine a type of error in case of a reduced speed. Therefore, much more sophisticated changes of the medical device's hardware implementation would be required. However, such changes are usually not feasible due to lengthy medical-device downtimes and huge additional costs in case of comprehensive hardware changes.

SUMMARY

The present disclosure proposes a system for detecting errors of a medical device by analyzing acoustic signals generated by a component of the medical device, the system comprising:

a sensor element arranged to detect a spectrum of noise or vibrations of a medical device to be supervised and to be arranged at the medical device to be supervised, a supervising element, whereby the sensor element and the supervising element may communicate with each other and thereby allow for provisioning of data corresponding to the acoustic signals, whereby the system further comprises a localized or distributed detection engine, the detection engine analyzing the data corresponding to the acoustic signals such that typical failures of each of a plurality of individual components of the medical device are distinguished, whereby the system further comprises a notification engine, the notification engine providing indications on the maintenance state of the medical device and/or one or more of the plurality of individual components of the medical device.

According to some embodiments, the disclosure proposes that the data corresponding to the acoustic signals is pre-processed to reduce the amount of data corresponding to the acoustic signals.

According to certain embodiments, the disclosure proposes that the sensor element is remote to the supervising element.

According to some embodiments, the disclosure proposes that the detection engine is based on at least one trained neural network.

In certain embodiments, the notification engine provides a maintenance state via a network interface.

In some embodiments, the detection engine is enabled to self-learning such that newly experienced failures of each of a plurality of individual components may be learned for future detection.

The disclosure also proposes a computer-implemented method for determining a maintenance state of a medical device comprising the steps of:

acquiring first acoustic data from an acoustic signal generated by the medical device and/or the medical device's components for (unsupervised/supervised) training a first and/or second machine-learning model, wherein the first machine-learning model is configured to generate an operation state of the medical device based on the acoustic data and wherein the first or second machine-learning model is configured to determine a maintenance state based on the operation state and the acoustic data.

acquiring second acoustic data from an acoustic signal generated by the medical device and/or the medical-device's components and generating via the first machine-learning model a present operation state of the medical device and/or the medical device's components.

determining in another step, via the first and/or the second machine-learning model a maintenance state of the medical device and/or the medical device's components, wherein the maintenance state is determined at least partly based on the second acoustic data and the generated operation state.

In some embodiments, the disclosure proposes that the computer-implemented method further comprises the step of providing a maintenance state via a network interface.

Further purposeful embodiments are subject to the specification and figure.

BRIEF DESCRIPTION OF THE DRAWINGS

In the following we will also refer to the figures for further describing the invention.

DETAILED DESCRIPTION

In the following we will make reference towards a medical device MD. A medical device may be any kind of medical device used for therapeutically treating a human or animal body. In particular, a medical device MD may be a device used for clearance of certain components of a body fluid such as blood. A medical device may be a treatment device, in particular, a medical device for blood purification, such as for renal replacement therapy or for hepatic support, including medical devices adapted for one or more of hemodialysis, hemodiafiltration, peritoneal dialysis, blood ultrafiltration, etc. Any such mentioning is to be understood as non-limiting if not explicitly marked as essential.

Also, in the following, data transport from one component to another component may be described. A data transport may be achieved by any kind of interface, including wired as well as wireless transport. As such any kind of 1-wire, SPI, USB, RS-232, IP, optical or any other appropriate transport scheme may be used as a means for a wired transport of data. As such any kind of Bluetooth, DECT, WLAN, ZigBee, mobile communication, such as LTE-LTE-A, and successor protocols may be used as a means for a wireless transport of data. Any such mentioning is to be understood as non-limiting if not explicitly marked as essential. It is to be noted that any such interface may not only be unidirectional but also bidirectional and may allow for updates of the firmware/software/computer—implemented method which does itself not alter the firmware of the medical device MD but allows for improved analysis/functionality due to a learning process.

Furthermore, even though not detailed in the following, it is assumed that data originating from one particular sensor element S may be distinguished from data of other sensor elements such that data of a particular sensor element S may be evaluated per sensor element. For such purpose, the data transport may be such that a unique identifier is used in the course of the transport or by associating a unique identifier to a certain set of data to be transferred.

Figure 1:
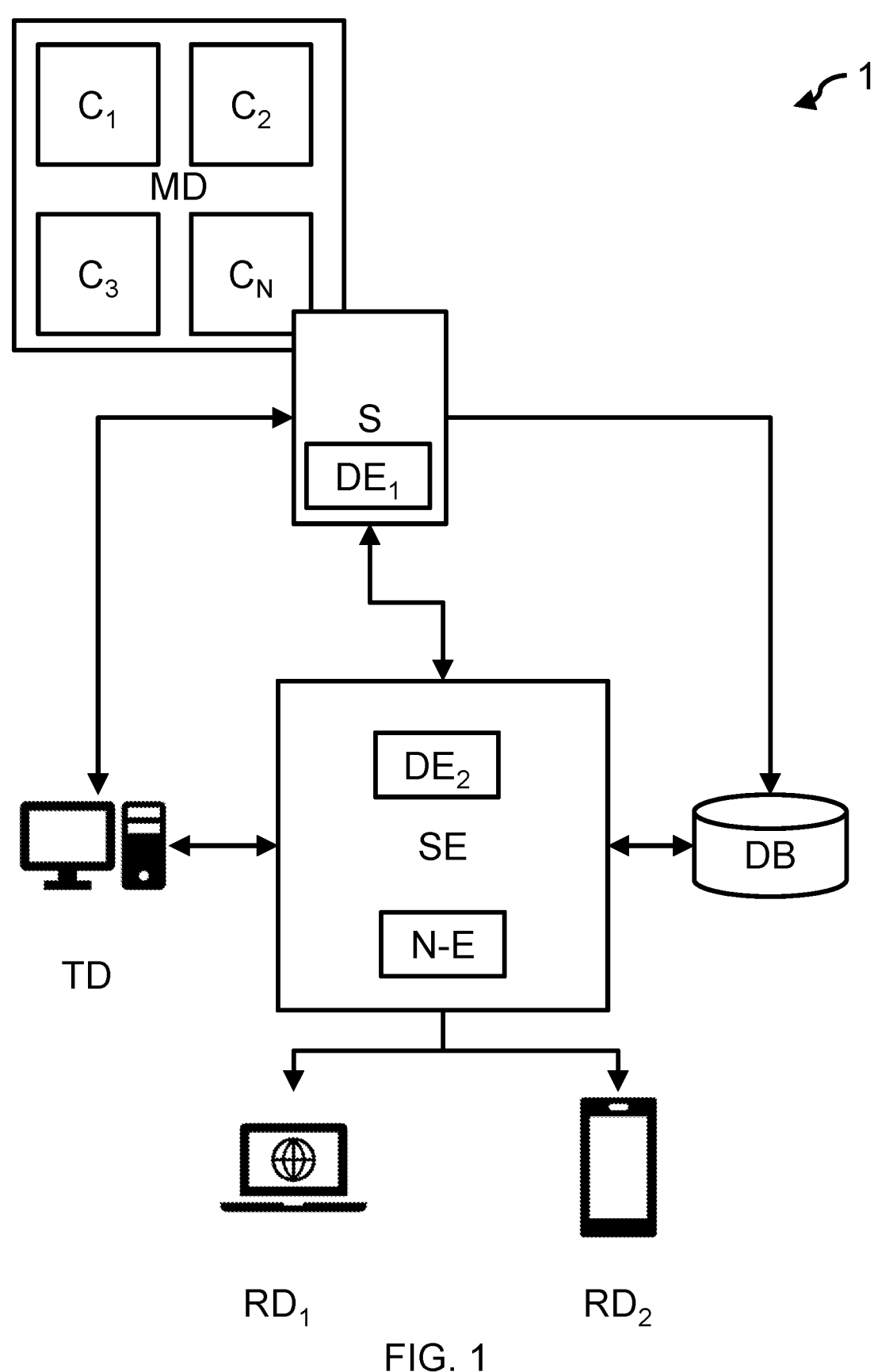
FIG. 1 shows a schematic overview of elements which may be involved in some embodiments.

According to embodiments, a system 1 for detecting errors of a medical device by analyzing acoustic signals generated by a component $C_1, C_2, C_3, \ldots C_N$ of the medical device MD is provided, see FIG. 1.

The component $C_1, C_2, C_3, \ldots C_N$ may be any kind of component which—when operating—may create either a distinctive sound or generate a distinctive vibration. The component $C_1, C_2, C_3, \ldots C_N$ is preferably an integral part of the medical device MD. For the purpose of understanding, it is noted that the actual number of components $C_1, C_2, C_3, \ldots C_N$ may vary from one type of medical device MD to another.

The system 1 further comprises a sensor element S arranged to detect a spectrum of noise or vibrations of a medical device MD to be supervised and to be arranged at the medical device MD to be supervised.

Figure 4:
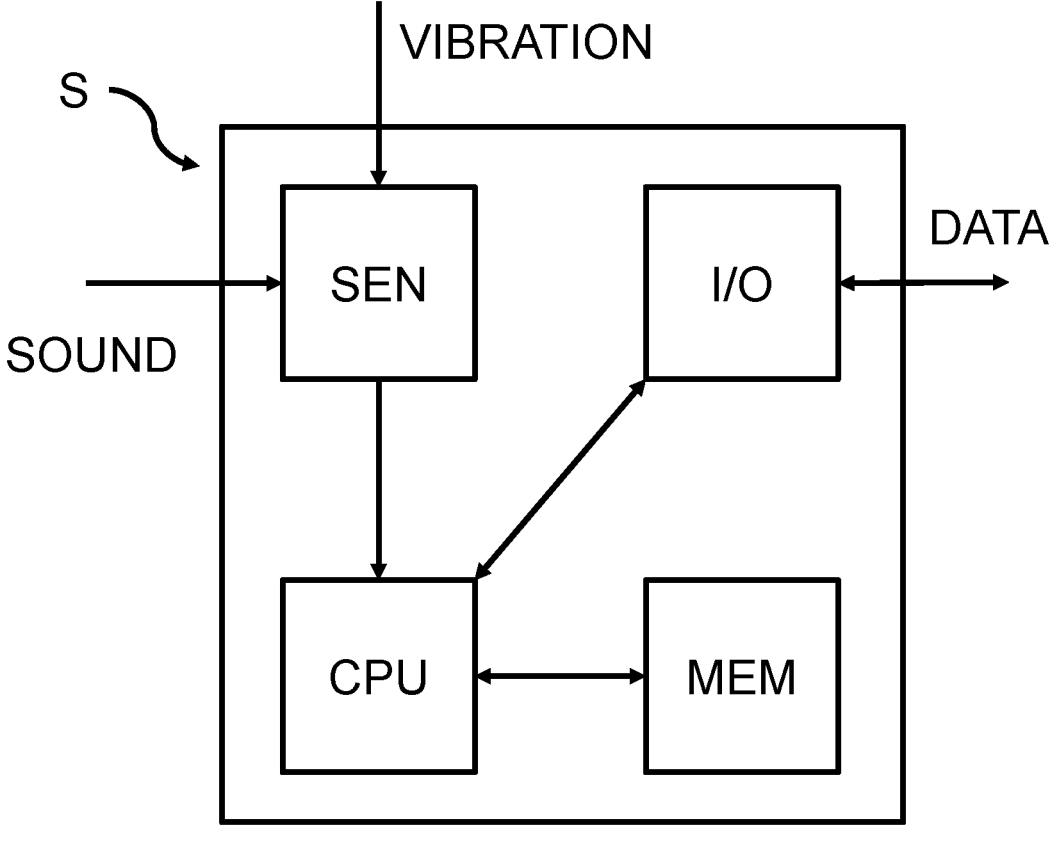
FIG. 4 shows a schematic overview of logical elements involved in some embodiments.

As shown in FIG. 4, the sensor element S may be any kind of a vibration detecting sensor and/or a sound detecting sensor SEN. For example, to provide for more reliable measurements, the sensor element S may be provided with a form-fitting housing such that it may be arranged relative to a certain type of medical device MD at a pre-known location, allowing for reproducible sounds/vibrations to be generated by the components $C_1, C_2, C_3, \ldots C_N$ when operating. It is also envisaged that the sensor element S may be affixed to a certain type of medical device MD, e.g., by using an (auxiliary) port arranged at the medical device MD. Assuming that the medical device MD is equipped with an RS-232 interface, one could envisage that the sensor element may be attached via a corresponding plug or socket towards the RS-232 interface. While for operation it is not necessary that there may be a data exchange via the interface, a data exchange may nevertheless be used in addition to collect further data to be transferred. The sensor element S may also comprise a memory MEM, such as RAM, and a processing entity, such as a microcontroller or a microprocessor, e.g., a RaspberryPI, a ESP8266, ARM or a DSP such as a TMS 320 based DSP as well as some kind of interface I/O providing connectivity either wired or wireless towards a supervising element SE or a Training Device TD detailed in the following. As such the sensor element S may not only perform acquisition of sensor data but may also store such data either directly or after processing in a memory MEM. Likewise, the processed or unprocessed data may also be provided via the interface towards other devices. Even though not detailed here, the sensor element S may also be enabled to preprocess and/or pre-evaluate data before passing data (either raw or processed) towards some other device.

As shown in FIG. 1, the system 1 further comprises a supervising element SE. The supervising element SE may be a workstation, such as a standard personal computer, server, or any other computing unit. The workstation may be enabled by software.

The sensor element S and the supervising element SE may communicate with each other and thereby allow for providing data corresponding to the acoustic signals. Data corresponding to the acoustic signals may also encompass vibrations detected by a vibration sensor. Also, the data may be subject to analog or digital filtering or any kind of other processing.

In addition, system 1 comprises a localized or distributed detection engine $DE_1$, $DE_2$. That is, while the detection engine $DE_2$ may be present mainly on the supervising element SE, it may be that a portion of the detection engine $DE_1$ allowing for some preprocessing may reside on the sensor element S. The detection engine is arranged for analyzing the data corresponding to the acoustic signals such that typical failures of each of a plurality of individual components $C_1, C_2, C_3, \ldots C_N$ of the medical device MD may be distinguished.

The system 1 further comprises a notification engine N-E, the notification engine N-E providing indications on the maintenance state of the medical device and/or one or more of the plurality of individual components $C_1, C_2, C_3, \ldots C_N$ of the medical device MD.

For example, it may be foreseen that the detection engine evaluates certain operating conditions indicating normal operation. For example, some medical devices may be used for different kinds of therapies, each one leading to unique sound and/or vibration characteristics. Hence, analyzing the data corresponding to the acoustic signals may reveal a certain type of normal operation. Information regarding such operation may be provided via the notification engine N-E, e.g., via a WWW-interface, a REST-interface, a Push Notification towards some database DB storing operational data, e.g., for determining maintenance intervals, and/or one or more remote devices $RD_1$, $RD_2$ such as a handheld device like a mobile phone having a specialized app or a web browser or being enabled to receive push-information or a general network interface such as an internet/intranet access, and/or a training device TD. Detection of an operating state may, in particular, be performed by a detection engine $DE_1$ located within the sensor element S. Likewise a more sophisticated analysis providing further insight whether a certain component is operating within normal conditions and if not, which error may be imminent, may be performed by a more powerful detection engine $DE_2$.

The database DB also allows for later-on-training on basis of actually experienced failures which were not detected before, thereby enhancing the detection.

Such analysis may be performed, e.g., by sufficiently trained neural networks, wherein the neural networks may be part of a computer-implemented method for determining a maintenance state of a medical device.

A computer-implemented method for determining a maintenance state of a medical device may comprise certain steps for training a machine-learning model.

Figures 2, 3:
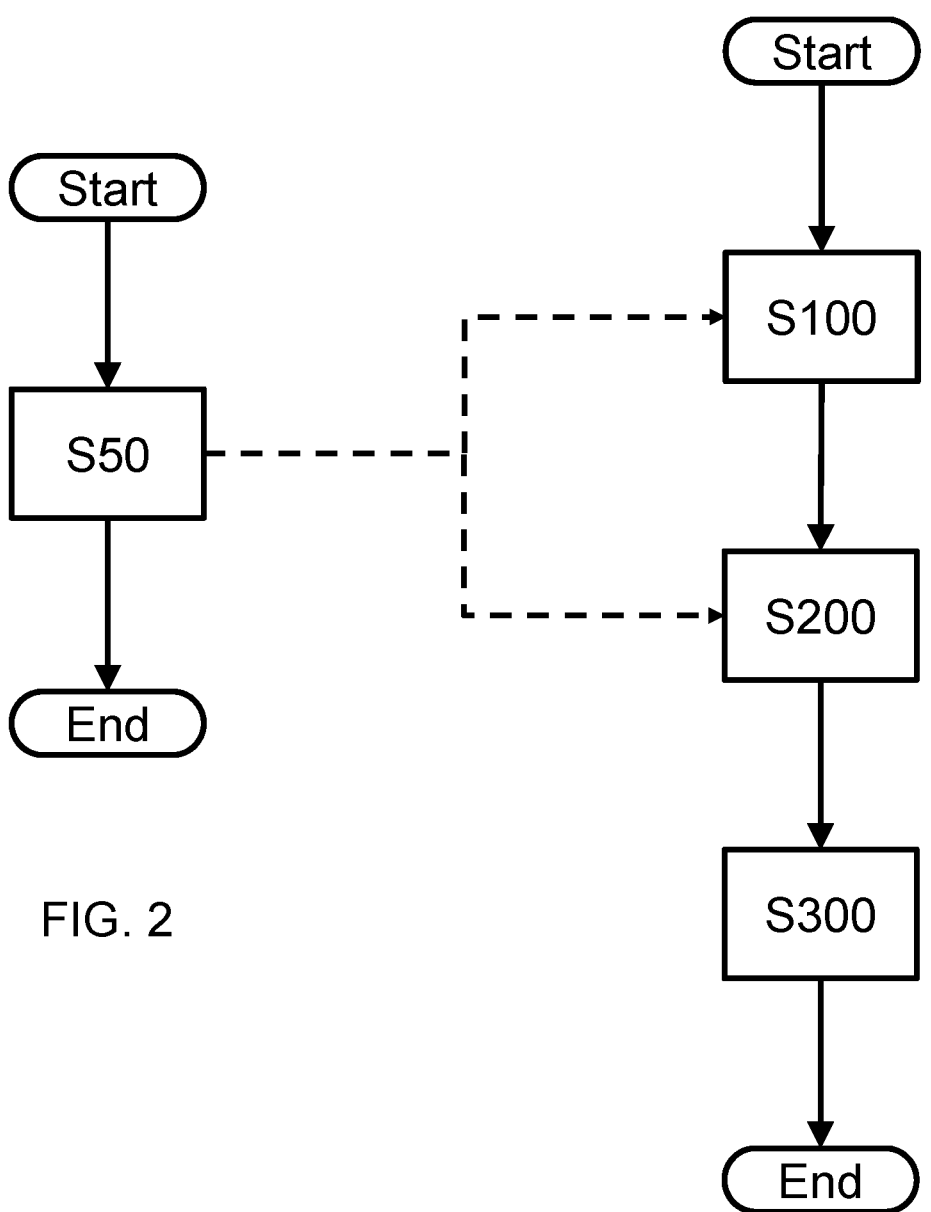
FIG. 2 shows schematically a flow chart of steps which may be involved in some embodiments during training.
FIG. 3 shows schematically a flow chart of steps which may be involved in some embodiments during operation.

In the example shown in FIG. 2, for example, the training comprises the step of acquiring S50 first acoustic data from an acoustic/vibration signal generated by the medical device MD and/or the medical device's components $C_1$, $C_2$, $C_3$, ... $C_N$ for unsupervised/supervised training a first and/or second machine-learning model.

As detailed above, a first machine-learning-model may be related to an operational state of a medical device respectively its medical device's components $C_1$, $C_2$, $C_3$, ... $C_N$. A second machine-learning model may be related to upcoming failures of any such component $C_1$, $C_2$, $C_3$, ... $C_N$.

To that end, one may envisage that acoustic/vibration signals are acquired in a training cycle and corresponding indications versus an operational status is attributed in a supervised training. This may also be used when servicing medical devices due to maintenance. In this connection, raw data as well as processed data may be forwarded to a training device TD. Upon detection of particular failures of one or more components $C_1$, $C_2$, $C_3$, ... $C_N$, a service technician may indicate to the training device TD the nature of the error. Once a respective first and/or second network is trained, it may be distributed towards one or more detection engines $DE_1$, $DE_2$ for use in an operational set-up.

For example, the first machine-learning model may configured to generate an operation state of the medical device MD based on the acoustic/vibration data.

Subject to the type of machine-learning, the first and/or second machine-learning model may be configured to determine a maintenance state based on the operation state and the acoustic/vibration data.

That is, even though separate networks may be envisaged, it may also be sufficient to only provide a single network offering both functionalities.

When the neural network(s) is/are trained, they may be used in an operational state as shown with respect to FIG. 3.

In a first step S100, second acoustic/vibration data is acquired from an acoustic/vibration signal 30 generated by the medical device MD and/or the medical device's components $C_1$, $C_2$, $C_3$, ... $C_N$ and via the first machine-learning model a present operation state of the medical device and/or the medical device's components is generated.

In another step S200, which might commence and/or end with respect to step S100 before, after or time-aligned, via the first and/or the second machine-learning model a maintenance state of the medical device MD and/or the medical device's components $C_1$, $C_2$, $C_3$, ... $C_N$ is determined.

According to some embodiments the notification engine NE provides a maintenance state via a network interface, e.g., within step S300.

The maintenance state is determined at least partly based on the second acoustic data and the generated operation state.

Data corresponding to the acoustic/vibration signals may be preprocessed, to reduce the amount of data corresponding to the acoustic/vibration signals.

Because the system 1 allows for the sensor element S to be remote to the supervising element SE, a number of sensor elements S may provide data to a single supervising element SE. Suppose for example a healthcare provider has different locations for the medical devices, e.g., in care homes, households, hospitals. Now a number of sensor elements S may be monitored by a single supervising element SE with respect to their operational status and in particular the maintenance status of certain components thereof. This allows, for example, for a technician to be deployed once a certain failure is upcoming.

For example, suppose that a motor $C_1$ creates a certain noise/vibration because of being hindered by dust, e.g., leading to a reduced rotation, or a fan $C_2$ howling, a tubing within a rotary pump $C_4$ squeaking, etc. Such suspicious motor noises/vibrations may indicate a serious condition to follow soon thereafter. In addition, operational data may also indicate that a certain element shall be replaced after a certain time of operation. While previously it may have been unnoticed before an actual failure happens, it will be easier to monitor operation as well as upcoming or actual errors, allowing for a quick response to solve the problem before an undesired condition may evolve or an unexpected medical-device downtime prevents a patient from receiving a prescribed medical treatment.

For example, detecting a failure of a compressor $C_1$ may be performed by an XGBoost model trained on various features extracted from vibration/sound data. Most prominent features used by the model may be (but not limited thereto) root mean square, a spectral skew and (larger) magnitudes of low frequency components, i.e., components within a range of e.g., 40-100 Hz. Frequency components may be provided from the vibration/sound data by (short time) Fourier transformation. Detecting grinding of a motor $C_1$ may likewise be performed by another or the same XGBoost model trained on various features extracted from vibration/sound data. Typically, motor grinding leads to (larger) magnitudes of high frequency components, i.e., components within a range of e.g., 800-1200 Hz. Again, frequency components may be provided from the vibration/sound data by (short time) Fourier transformation. Likewise, a slipping motor $C_1$ typically is indicated by a squeaking noise, which typically occurs intermittently and lasts for only a short duration (e.g., around 0.2 seconds). Various mid-range frequencies may contribute to the identification of these patterns. Again, detection may be performed by another or the same XGBoost model, e.g., with bidirectional lead and lagged feature inputs. While these failures represent the more common ones, other failures, which may be lot dependent, are less common. However, using a bidirectional long-short-term-memory-type for the neural network(s) to learn a normal operational pattern via self-supervised learning allows anomalous sounds to be flagged.

To this end, XGBoost is an open-source software library that implements optimized distributed gradient boosting machine learning algorithms under the Gradient Boosting framework. XGBoost stands for Extreme Gradient Boosting, is a scalable, distributed gradient-boosted decision tree (GBDT) machine learning library. It provides parallel tree boosting and is the leading machine learning library for regression, classification, and ranking problems. It is to be noted that the use of XGBoost is of exemplary nature and does not disqualify other machine-learning models to be used for the purpose of the disclosure. In particular, the disclosure envisages the usage of feature segmentation within self-supervised learning as it is known from the field of speech recognition such as Wave2Vec neural networks. Such approach allows to separate data from healthy and faulty components without the necessity of manual labeling, i.e., unsupervised.

As hinted above according to embodiments, the detection engines $DE_1$, $DE_2$ may be based on at least one trained neural network.

Such neural network may be a convolutional network employing e.g., short time Fourier transformation, root mean square and other techniques (e.g., as part of $DE_1$). Furthermore, the neural network(s) may be convolutional networks. Training may be performed with a sliding window, e.g., with respect to a sound spectrogram (e.g., as provided by short term Fourier transformation). Data may be split into segments to create component-specific fingerprints and failure detection models, e.g., for the compressor, the motor . . . or any other component $C_1$, $C_2$, $C_3$, . . . $C_N$. In particular, the detection engine(s) $DE_1$, $DE_2$ are able to handle concurrent component runs.

It is also envisaged to use an autoencoder to reconstruct data. An autoencoder compresses (encodes) input to lower dimensionality (code) and uses this for the reconstruction (decode) of new samples. While healthy components lead to lower reconstruction errors, it is to be noticed that unhealthy components in turn lead after reconstruction to a higher reconstruction error. Hence, already a simple threshold with respect to the reconstruction error may be indicative of an upcoming failure. More sophisticated methods may be based on a mean-square error histogram which e.g., in case of an unhealthy component shows with respect to a like histogram of a same but healthy component a right skewed error distribution.

The maintenance state is determined at least partly on acoustic data from an acoustical signal emitted from the medical device and/or at least one of the medical device's components.

In one example, the "raw" acoustic/vibration data, i.e., the acoustic/vibration data as received from a sensing device (microphone, vibration sensor) of the maintenance-detection system, is transformed first into a time-frequency representation. The time-frequency representation then allows to process the acoustic data as image data. In this case, the first machine-learning model for generating an operation state based on acoustic data can include a convolutional neural network (CNN) or at least a convolutional-neural-network layer of a more complex machine-learning algorithm. CNNs are often employed for image data due to their high precision in classifying images compared to other types of neural networks.

Determining a maintenance state of the medical device and/or the medical device's components $C_1$, $C_2$, $C_3$, . . . $C_N$ based at least partly on second acoustic data and the generated operation state can be performed by means of the first or a second machine-learning model. For example, the first machine-learning model can include several modules/layers, wherein the modules/layers process the data "all at once", i.e., the generated operation state of the medical device/components remain "hidden", wherein the "hidden" operation state is further processed to determine a final maintenance state. In another example, the output of the first machine-learning model (e.g., the operation state) is stored and transferred to a second machine-learning model.

The second machine-learning model can comprise one or more machine-learning algorithms to process, e.g., filter and/or classify, the acoustic data and the generated operation state of the medical device. In one aspect, the second machine-learning model can include supervised tree-based algorithms such as an XGBoost model for extracting features from the acoustic data. For example, the result of the first machine-learning model generates an operation state that indicates a presently active compressor of a PD device.

Then, the trained second machine-learning model, e.g., an XGBoost model, can analyze the acoustic data of the compressor by comparing the actual acoustic data of the compressor with acoustic patterns of faulty compressors as trained. Such tree-based algorithms can also be employed for any other medical device components to detect, e.g., motor slipping or motor grinding.

The second machine-learning model may also include any unsupervised/self-supervised machine-learning algorithm wherein the unsupervised/self-supervised machine-learning algorithm may detect faulty components based on any acoustic deviation from "healthy" acoustic patterns of a medical device or a medical device component. In one example, a bidirectional long-short-term-memory (LSTM) neural-network model is employed, wherein anomalous sounds are flagged as unusual, i.e., sounds which do not occur during normal device operation. Other unsupervised/self-supervised machine-learning algorithms may employ autoencoders to determine a reconstruction error wherein the reconstruction error can be constructed as a measure for faulty medical device components.

According to some embodiments, the detection engine $DE_1$, $DE_2$ is enabled to self-learning such that newly experienced failures of each of a plurality of individual components may be learned for future detection.

The first and/or second machine-learning model may run on the sensor element S and/or on a remote computing unit, e.g., an external server such as the supervising element SE. It is also possible that some computations are performed on the local computing unit CPU of the sensor element S, e.g., the computing of short-time Fourier transformed acoustic/vibration data. In case of the supervising element SE, the sensor element S can include a network gateway (modem, router) I/O, wherein the network gateway I/O allows communication with a local network and/or wide-area network. With that, calculations requiring high computational resources can quickly be performed on suited remote hardware.

A maintenance state can be determined for any of the medical devices MD or the medical devices' components wherein the maintenance state comprises information of the proper working of the medical device and/or its components, e.g., the medical device and its components $C_1$, $C_2$, $C_3$, . . . $C_N$ work safely and perform effective and error-free treatments according to a given prescription. The maintenance state can be displayed on any external computing device (via a computer, smartphone, or tablet) $RD_1$, $RD_2$, e.g., via a web application, wherein the computing device is in communication with the maintenance-detection system using wireless/wired communication means (Wi-Fi, Ethernet, . . . ).

The maintenance state can be depicted, e.g., as any sort of data table, list, or figure comprising information regarding the proper working of the medical device and the medical device's components. For example, properly working components may be displayed as "OK", wherein non-properly working components may be marked as "NOT OK/NOK". The maintenance state may also include more detailed information, e.g., the raw acoustic data from the acoustic signal of the medical device MD and/or intermediary results from the first and/or second machine-learning model. In one example, final results or intermediary results of any of the machine-learning models can be depicted as graphics or any other type of visualization.

Moreover, the maintenance state may comprise a present maintenance-state portion, i.e., the proper working of the medical device MD and its components $C_1$, $C_2$, $C_3$, . . . $C_N$ of a present inspection, and/or a future maintenance-state portion, i.e., the proper working of the medical device and its components at a later point in time. For example, a present maintenance-state portion of a component can be displayed as "OK" but the future maintenance-state portion, e.g., the predicted maintenance state in four weeks, may show a "NOK". A prediction algorithm may comprise a machine-learning algorithm based on a neural network, wherein the machine-learning algorithm may be included in the first and/or second machine-learning model. With that, faulty components can timely be detected so that uncontrolled medical device downtimes or hazardous situations for patients are prevented.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A system for detecting errors of a medical device by analyzing acoustic or vibration signals generated by at least one component of the medical device, the system comprising:

a sensor element arranged to detect a spectrum of noise or vibrations of the medical device and to be arranged at the medical device, a supervising element, whereby the sensor element and the supervising element are adapted to communicate with each other and thereby allow for data corresponding to the acoustic signals to be transmitted between the sensor element and the supervising element, a localized or distributed detection engine, the detection engine adapted to analyze the data corresponding to the acoustic signals such that typical failures of each of a plurality of individual components of the medical device are distinguished, wherein the detection engine is configured to:

generate an operation state of the at least one component of the medical device via a first machine-learning model based on the acoustic signals, wherein the operation state is indicative of a type of treatment being performed by the medical device; and determine a maintenance state of the at least one component of the medical device via a second machine-learning model based on the operation state and the acoustic signals; and a notification engine adapted to provide indications on the maintenance state of the medical device or one or more of the plurality of individual components of the medical device.

2. The system according to claim 1, whereby the data corresponding to the acoustic or vibration signals is preprocessed to thereby reduce the amount of data corresponding to the acoustic signals.

3. The system according to claim 1, whereby the sensor element is remote to the supervising element.

4. The system according to claim 1, whereby the detection engine is based on at least one trained neural network.

5. The system according to claim 1, whereby the notification engine is adapted to provide a maintenance state via a network interface.

6. The system according to claim 1, whereby the detection engine is enabled to self-learn such that newly experienced failures of each of a plurality of individual components may be learned for future detection.

7. A computer-implemented method for determining a maintenance state of a medical device or components of the medical device, the method comprising:

acquiring first acoustic data or first vibration data from a first acoustic signal or a first vibration signal generated by the medical device or the components of the medical device for training a first machine-learning model, wherein the first machine-learning model is configured to generate an operation state of the medical device or components of the medical device based on the first acoustic data or the first vibration data, wherein the operation state is indicative of a type of treatment being performed by the medical device, and wherein a second machine-learning model is configured to determine the maintenance state of the medical device or the components of the medical device based on the operation state and the first acoustic data or the first vibration data;

acquiring second acoustic data or second vibration data from a second acoustic signal or a second vibration signal generated by the medical device or the components of the medical device and generating via the first machine-learning model a present operation state of the medical device or the components of the medical device, wherein the present operation state is indicative of a present type of treatment being performed by the medical device; and determining via the second machine-learning model the maintenance state of the medical device or the components of the medical device;

wherein the maintenance state is determined at least partly based on (i) the second acoustic data or the second vibration data and (ii) the present operation state generated by the first machine-learning model.

8. The computer-implemented method according to claim 7, further comprising providing the maintenance state via a network interface.

9. The computer-implemented method according to claim 7, wherein the training is unsupervised.

10. The computer-implemented method according to claim 7, wherein the first machine-learning model is configured to determine the maintenance state based on the operation state and the second acoustic data or the second vibration data, and wherein the determination of the maintenance state of the medical device or the components of the medical device is performed via the first machine-learning model.

11. The computer-implemented method according to claim 7, wherein acquiring the first acoustic data or first vibration data comprises extracting features from the first acoustic data or first vibration data, wherein the features include at least one of: a root mean square, a spectral skew, and magnitudes.

12. The computer-implemented method according to claim 7, wherein acquiring the first acoustic data or first vibration data comprises splitting the first acoustic data or first vibration data into segments to create component-specific fingerprints and failure detection models.

13. The computer-implemented method according to claim 7, wherein the first machine-learning model is based on a mean-square error histogram of previous acoustic data or previous vibration data.

14. The computer-implemented method according to claim 7, wherein acquiring the second acoustic data or second vibration data comprises transforming the second acoustic data or second vibration data into a time-frequency representation.

15. A medical device adapted for dialysis treatment, the medical device comprising:

a sensor element arranged to detect a spectrum of noise or vibrations of the medical device, a supervising element, whereby the sensor element and the supervising element are adapted to communicate with each other and thereby allow for data corresponding to the acoustic signals to be transmitted between the sensor element and the supervising element, a localized or distributed detection engine, the detection engine adapted to analyze the data corresponding to the acoustic signals such that typical failures of each of a plurality of individual components of the medical device are distinguished, wherein the detection engine is configured to:

generate an operation state of the at least one component of the medical device via a first machine-learning model based on the acoustic signals, wherein the operation state is indicative of a type of treatment being performed by the medical device; and determine a maintenance state of the at least one component of the medical device via a second machine-learning model based on the operation state and the acoustic signals; and a notification engine adapted to provide indications on the maintenance state of the medical device or one or more of the plurality of individual components of the medical device.

16. The medical device according to claim 15, whereby the data corresponding to the acoustic or vibration signals is preprocessed to thereby reduce the amount of data corresponding to the acoustic signals.

17. The medical device according to claim 15, whereby the sensor element is remote to the supervising element.

18. The medical device according to claim 15, whereby the detection engine is based on at least one trained neural network.

19. The medical device according to claim 15, whereby the notification engine is adapted to provide a maintenance state via a network interface.

20. The medical device according to claim 15, whereby the detection engine is enabled to self-learn such that newly experienced failures of each of a plurality of individual components may be learned for future detection.

* * * * *